(12) United States Patent
Armacost et al.

(10) Patent No.: US 11,642,224 B2
(45) Date of Patent: May 9, 2023

(54) IMPLANT AND METHOD FOR ANKLE SYNDEMOSIS TREATMENT

(71) Applicant: WRIGHT MEDICAL TECHNOLOGY, INC., Memphis, TN (US)

(72) Inventors: Scott A. Armacost, Germantown, TN (US); Sach Combs, Salt Lake City, UT (US); Murray John Penner, Vancouver (CA); Bruce E. Cohen, Charlotte, NC (US); Bryan D. Den Hartog, St. Paul, MN (US); Gregory C. Berlet, Westerville, OH (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 203 days.

(21) Appl. No.: 16/896,657

(22) Filed: Jun. 9, 2020

(65) Prior Publication Data

US 2020/0297502 A1 Sep. 24, 2020

Related U.S. Application Data

(63) Continuation of application No. 15/586,694, filed on May 4, 2017, now Pat. No. 10,709,566.

(51) Int. Cl.
*A61F 2/42* (2006.01)
*A61B 17/80* (2006.01)
(Continued)

(52) U.S. Cl.
CPC ........ *A61F 2/4225* (2013.01); *A61B 17/0401* (2013.01); *A61B 17/683* (2013.01);
(Continued)

(58) Field of Classification Search
CPC .................. A61F 2/4202; A61F 2/4225; A61F 2002/30462; A61F 2002/4235;
(Continued)

(56) References Cited

U.S. PATENT DOCUMENTS 5,364,399 A * 11/1994 Lowery .............. A61B 17/1728
606/295
6,716,234 B2 4/2004 Grafton et al.
(Continued)

FOREIGN PATENT DOCUMENTS

EP 0705572 B1 1/2002
EP 2455002 A1 5/2012
(Continued)

OTHER PUBLICATIONS

Second Examination Report issued in connection with corresponding Australian Patent Application No. 2019208234, dated Apr. 7, 2019, 6 pages.
(Continued)

*Primary Examiner* — Marcela I. Shirsat
(74) *Attorney, Agent, or Firm* — Duane Morris LLP

(57) ABSTRACT

An implant includes a curved first plate section having a curvature about a longitudinal axis extending in a longitudinal direction. The first plate section has a first hole and a second hole. The first hole and the second hole are positioned to receive respective bone screws for attaching the implant to a first curved surface of a bone having a syndesmosis. A second plate section extends continuously from the first plate section. The second plate section has at least a third hole that is positioned to be offset from the first hole and the second hole in a direction that is anterior or posterior from the first hole and the second hole in a case where the longitudinal axis is aligned along a superior-inferior direction. The third hole is configured to receive at least one
(Continued)

screw or at least one button for holding a suture at a position offset from the first line segment hole and the second hole in the anterior or posterior direction, for reducing the syndesmosis.

4 Claims, 7 Drawing Sheets

(51) Int. Cl.
*A61B 17/04* (2006.01)
*A61B 17/86* (2006.01)
*A61B 17/68* (2006.01)
*A61F 2/30* (2006.01)

(52) U.S. Cl.
CPC .......... *A61B 17/80* (2013.01); *A61B 17/8052* (2013.01); *A61B 17/8061* (2013.01); *A61B 17/86* (2013.01); *A61B 2017/044* (2013.01); *A61B 2017/0404* (2013.01); *A61B 2017/8655* (2013.01); *A61F 2/4202* (2013.01); *A61F 2002/30462* (2013.01); *A61F 2002/4233* (2013.01)

(58) Field of Classification Search
CPC ... A61B 17/0401; A61B 17/683; A61B 17/80; A61B 17/8061; A61B 17/8052; A61B 17/86; A61B 2017/564; A61B 2017/0404; A61B 2017/044; A61B 2017/8655
USPC ................. 606/280, 286, 291, 70; 623/21.18
See application file for complete search history.

(56) References Cited

U.S. PATENT DOCUMENTS

| | | |
|---|---|---|
| 7,655,029 B2 | 2/2010 | Niederberger et al. |
| 8,523,921 B2 | 9/2013 | Horan et al. |
| 9,259,252 B2 | 2/2016 | Kay et al. |
| 2004/0102777 A1 | 5/2004 | Huebner |
| 2005/0049594 A1 | 3/2005 | Wack et al. |
| 2005/0261688 A1 | 11/2005 | Grady, Jr. et al. |
| 2007/0123880 A1 | 5/2007 | Medoff |
| 2008/0300637 A1 | 12/2008 | Austin et al. |
| 2009/0234462 A1 | 9/2009 | Mullaney et al. |
| 2010/0030276 A1 | 2/2010 | Huebner et al. |
| 2010/0256687 A1 | 10/2010 | Neufeld |
| 2012/0123474 A1* | 5/2012 | Zajac ................. A61B 17/8061 606/232 |
| 2013/0090694 A1 | 4/2013 | Norris |
| 2013/0172942 A1 | 7/2013 | Lewis et al. |
| 2014/0107798 A1* | 4/2014 | Jeng ..................... A61B 17/808 623/21.18 |
| 2014/0277178 A1 | 9/2014 | O'Kane et al. |
| 2015/0051601 A1* | 2/2015 | Larsen .................. A61B 17/82 606/74 |
| 2015/0327899 A1 | 11/2015 | Early et al. |
| 2016/0262814 A1* | 9/2016 | Wainscott .......... A61B 17/8061 |
| 2016/0278828 A1 | 9/2016 | Ragghianti |
| 2016/0310183 A1 | 10/2016 | Shah et al. |

FOREIGN PATENT DOCUMENTS

| | | |
|---|---|---|
| JP | 2008500143 A | 1/2008 |
| WO | 2007103333 A2 | 9/2007 |
| WO | 2017062300 A1 | 4/2017 |

OTHER PUBLICATIONS

Office Action issued in connection with corresponding Japanese Patent Application No. 2018-084013, dated May 14, 2019, 9 pages.
Examination Report No. 2 issued for corresponding Australian Patent Application No. 2018202727, dated Dec. 21, 2018, 12 pages.
Regauer, Markus, et al., "Syndesmotic InternalBrace for Anatomic Distal Tibiofibular Ligament Augmentation", World Journal of Orthopedics, published online Apr. 18, 2017, vol. 8, Issue 4, pp. 301-309, retrieved from internet on Dec. 2018, <URL: https://www.ncbi.nlm.nih.gov/pmc/articles/PMC5396014/>.
Search Report issued for corresponding European Patent Application No. 18169251.8, dated Sep. 19, 2018, 11 pages.
Examination Report No. 1 issued for corresponding Australian Patent Application No. 2018202727, dated Aug. 17, 2018, 14 pages.
Arthrex: Foot and Ankle What's New for Sports Surgeons [Viewed on internet on Aug. 16, 2018], <URL: https://www.youtube.com/watch?v=GFbUyQuTz88> Published May 5, 2015.
Kennedy, M.T. et al. "A computed tomography evaluation of two hundred normal ankles, to ascertain what anatomical landmarks to use when compressing or placing an ankle syndesmosis screw", The Foot 24, 2014, 157-160.
Arthrex TightRope Syndesmosis Fixation, Surgical Technique, 2012, 8 pages.
ZipTight Fixation System, Ankle Syndesmosis Surgical Protocol by Timothy Charlton, M.D., BIOMET Sports Medicine, undated, 8 pages.
Fourth Examination Report issued in connection with corresponding Australian Patent Application No. 2019208234, dated Nov. 10, 2020, 4 pages.
Office Action issued in connection with corresponding Canadian Patent Application No. 3,001,376, dated Jul. 28, 2020, 4 pages.
First Examination Report issued in connection with corresponding Australian Patent Application No. 2020286239, dated Jul. 14, 2022, 5 pages.

* cited by examiner

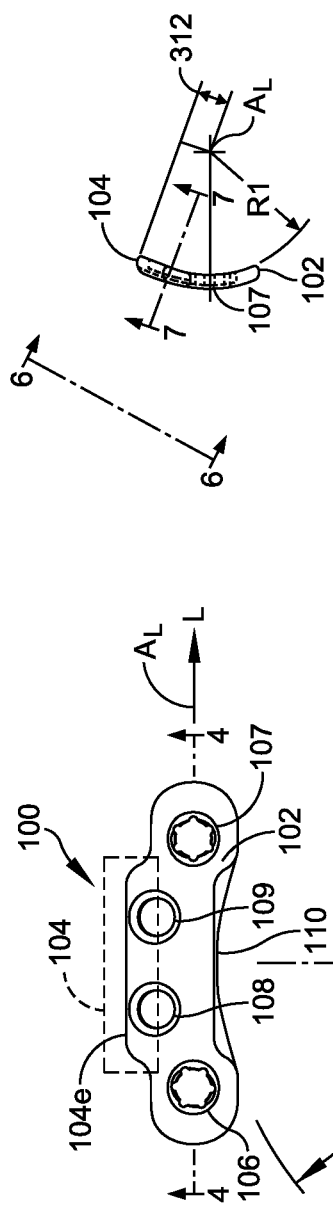
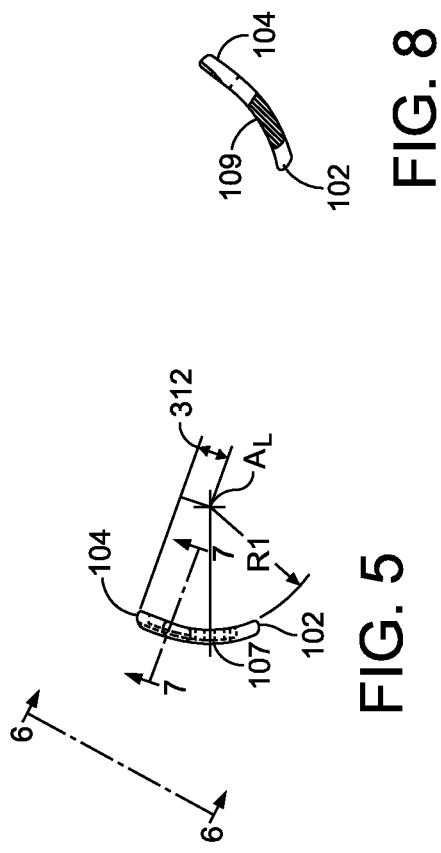
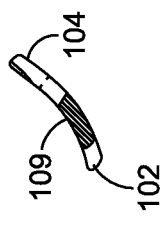
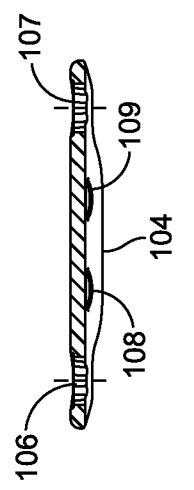
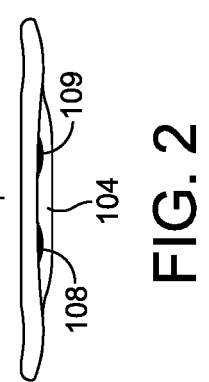
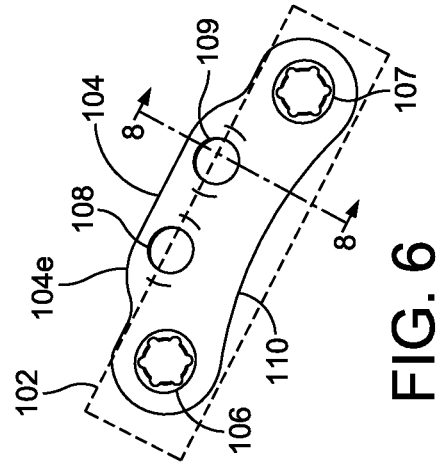

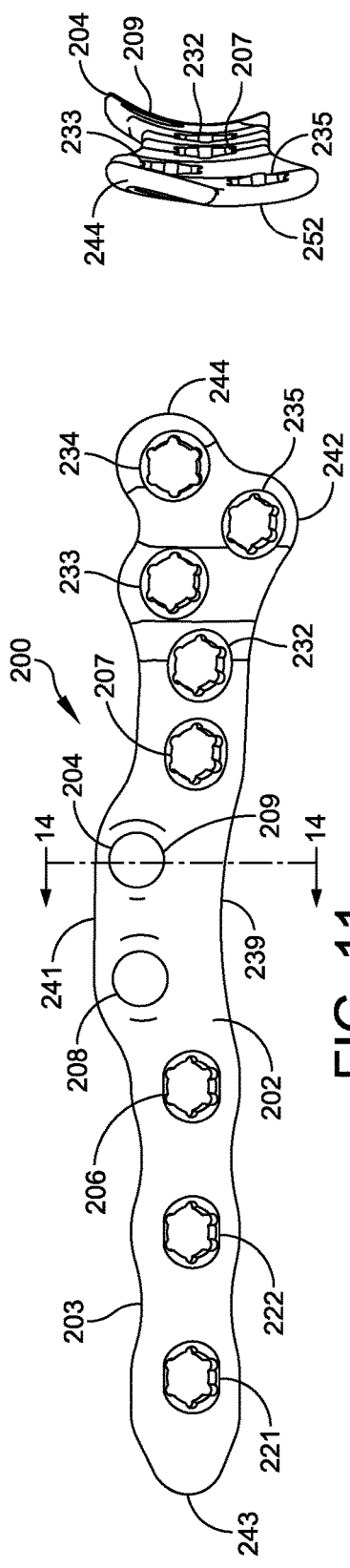
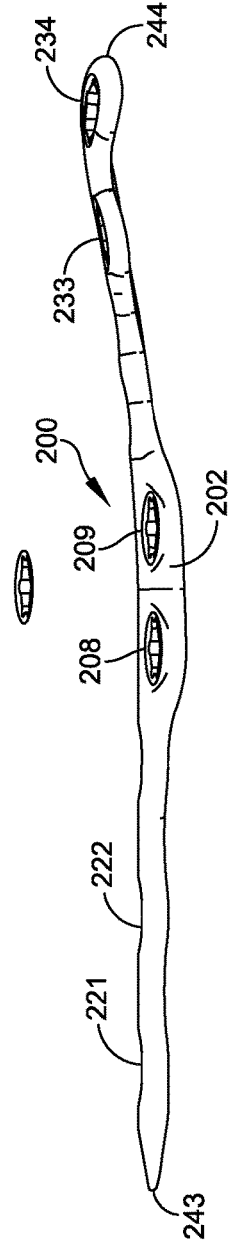
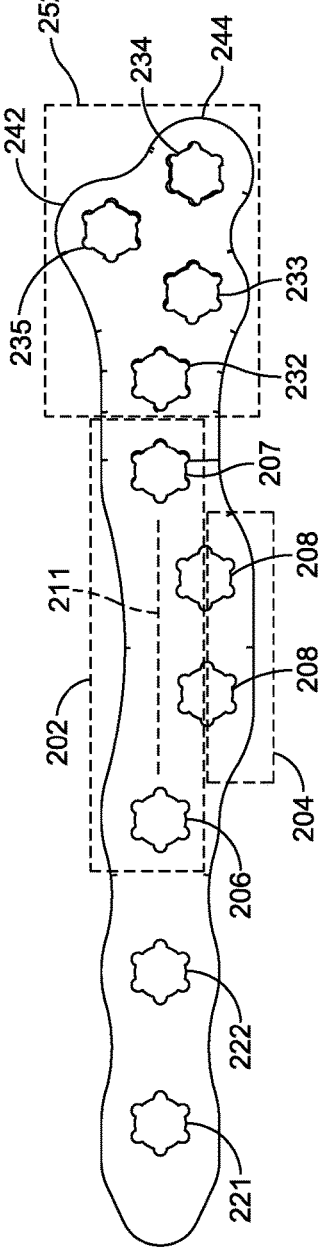

ically may require surgery. Surgical methods can include implantation of syndesmosis screws or tensioned sutures through the fibula and tibia to reduce the syndesmosis.

IMPLANT AND METHOD FOR ANKLE SYNDEMOSIS TREATMENT

This application is a continuation of patent application Ser. No. 15/586,694, filed May 4, 2017, the entirety of which is incorporated herein by reference.

FIELD

This disclosure relates to implants for treatment of ankle syndesmosis injuries.

BACKGROUND

A syndesmosis is a joint where two bones are held together by thick connective ligaments. For example, the lower ends of the tibia and fibula are connected by the ankle syndesmosis. An ankle syndesmosis injury (high ankle sprain) involves one or more of the ligaments connecting the bottom ends of the tibia and fibula. A high ankle sprain stretches or tears one of these ligaments. A syndesmosis injury involves a stretching or tear in one of the ligaments in the ankle syndesmosis and can lead to ankle instability. In severe tears of the ligaments, the ends of the tibia and fibula can spread apart. Syndesmosis injuries that cause ankle instability may require surgery. Surgical methods can include implantation of syndesmosis screws or tensioned sutures through the fibula and tibia to reduce the syndesmosis.

SUMMARY

In some embodiments, an implant, comprises a curved first plate section having a curvature about a longitudinal axis extending in a longitudinal direction. The curved first plate section has a first hole and a second hole. The first hole and the second hole are positioned to receive respective bone screws for attaching the implant to a first curved surface of a bone having a syndesmosis. A second plate section extends continuously from the curved first plate section. The second plate section has at least a third hole offset in a direction that is anterior or posterior from the first hole and the second hole in a case where the longitudinal axis is aligned along a superior-inferior direction. The third hole is configured to receive at least one screw or at least one button for holding a suture at a position offset in the posterior direction from the first line hole and the second hole, for reducing the syndesmosis.

In some embodiments, an implant system comprises: a bone plate comprising a curved first plate section having a curvature about a longitudinal axis extending in a longitudinal direction. The curved first plate section subtends an angle from 5 degrees to 45 degrees. The curved first plate section has a first hole and a second hole arranged along a first line segment parallel to the longitudinal axis. The first hole and the second hole are positioned to receive respective bone screws for attaching the implant to a curved surface of a fibula that extends to an ankle having a syndesmosis. A second plate section extends continuously from the curved first plate section. The second plate section has a third hole offset from the first line segment in a direction that is anterior or posterior from the first hole and the second hole in a case where the longitudinal axis is aligned along a superior-inferior direction. The third hole is configured to receive at least one bone screw or button for holding a suture. A third plate section is located adjacent the second hole and having a concave region shaped to conform to a lateral malleolus of the fibula. The third plate section has at least a fourth hole positioned to receive an additional bone screw. The system also includes at least one suture and at least one fastener including a bone screw or a button for positioning the at least one suture at a lateral apex of the fibula for reducing the syndesmosis.

In some embodiments, a method comprises: implanting a bone plate on an anterolateral side of a fibula having a syndesmosis, the bone plate having: a curved plate section having a curvature about a longitudinal axis extending in a longitudinal direction, the curved plate section having a first superior hole and a first inferior hole, the first superior hole and the first inferior hole positioned to receive respective bone screws for attaching the implant to an anterolateral surface of a fibula that extends to an ankle, and a lateral plate section extending continuously from the curved plate section, the lateral plate section having at least one syndesmosis hole offset in a posterior direction from the first superior hole and a first inferior hole, the at least one syndesmosis hole configured to receive at least one screw or button for holding at least one suture at a lateral apex of the fibula; inserting the at least one suture through the at least one syndesmosis hole, the fibula, and a centroid of a tibia adjacent the fibula; and tensioning the suture to reduce the syndesmosis.

In some embodiments, an implant, comprises a curved first plate section having a curvature about a longitudinal axis extending in a longitudinal direction. The curved first plate section has a first hole and a second hole. The first hole and the second hole are positioned to receive respective bone screws for attaching the implant to a first curved surface of a bone having a syndesmosis. A second plate section extends continuously from the curved first plate section. The second plate section has at least a third hole offset in a tangential direction from the first hole and the second hole, wherein the tangential direction is orthogonal to the longitudinal direction and a radial direction. The third hole is configured to receive at least one screw or button for holding a suture at a position offset in the tangential direction from the first line hole and the second hole, for reducing the syndesmosis.

BRIEF DESCRIPTION OF THE DRAWINGS

FIG. 1 is an anterolateral view of an embodiment of a syndesmosis plate.

FIG. 2 is an anterior edge view of the syndesmosis plate of FIG. 1.

FIG. 3 is a medial view of the syndesmosis plate of FIG. 1.

FIG. 4 is a cross-sectional view of the implant of FIG. 1, taken across section line 4-4 of FIG. 1.

FIG. 5 is a superior end view of the syndesmosis plate of FIG. 1.

FIG. 6 is a lateral view of the syndesmosis plate of FIG. 1.

FIG. 7 is a cross-sectional view of the implant of FIG. 5, taken across section line 7-7 of FIG. 5.

FIG. 8 is a cross-sectional view of the implant of FIG. 6, taken across section line 8-8 of FIG. 6.

FIG. 10 is an edge view of an embodiment of a fibula fracture plate.

FIG. 11 is a lateral view of the fibula fracture plate of FIG. 10.

FIG. 12 is a medial view of the fibula fracture plate of FIG. 10.

FIG. 13 is an inferior view of the fibula fracture plate of FIG. 10.

FIG. 14 is a cross-sectional view of the implant of FIG. 11, taken across section line 14-14 of FIG. 11.

DETAILED DESCRIPTION

Figure 9:
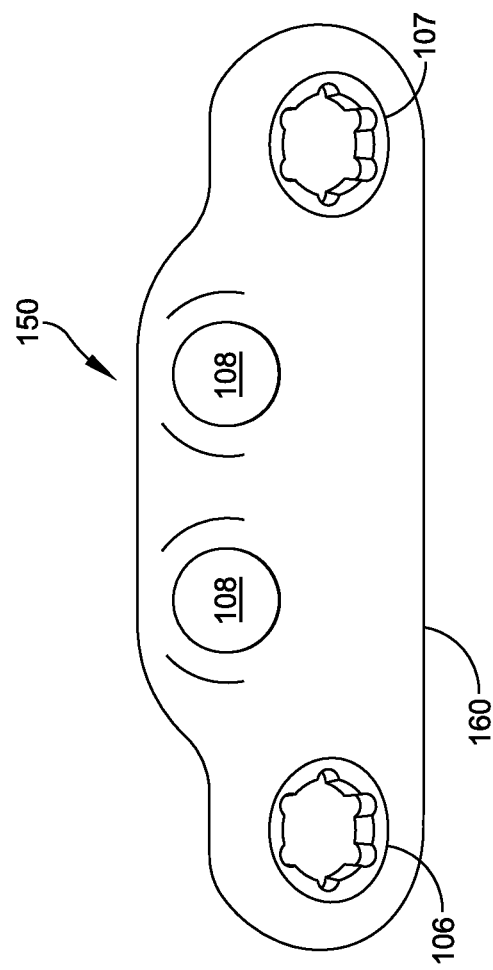
FIG. 9 is a lateral view of a variation of the syndesmosis plate of FIG. 1.
Figure 15:
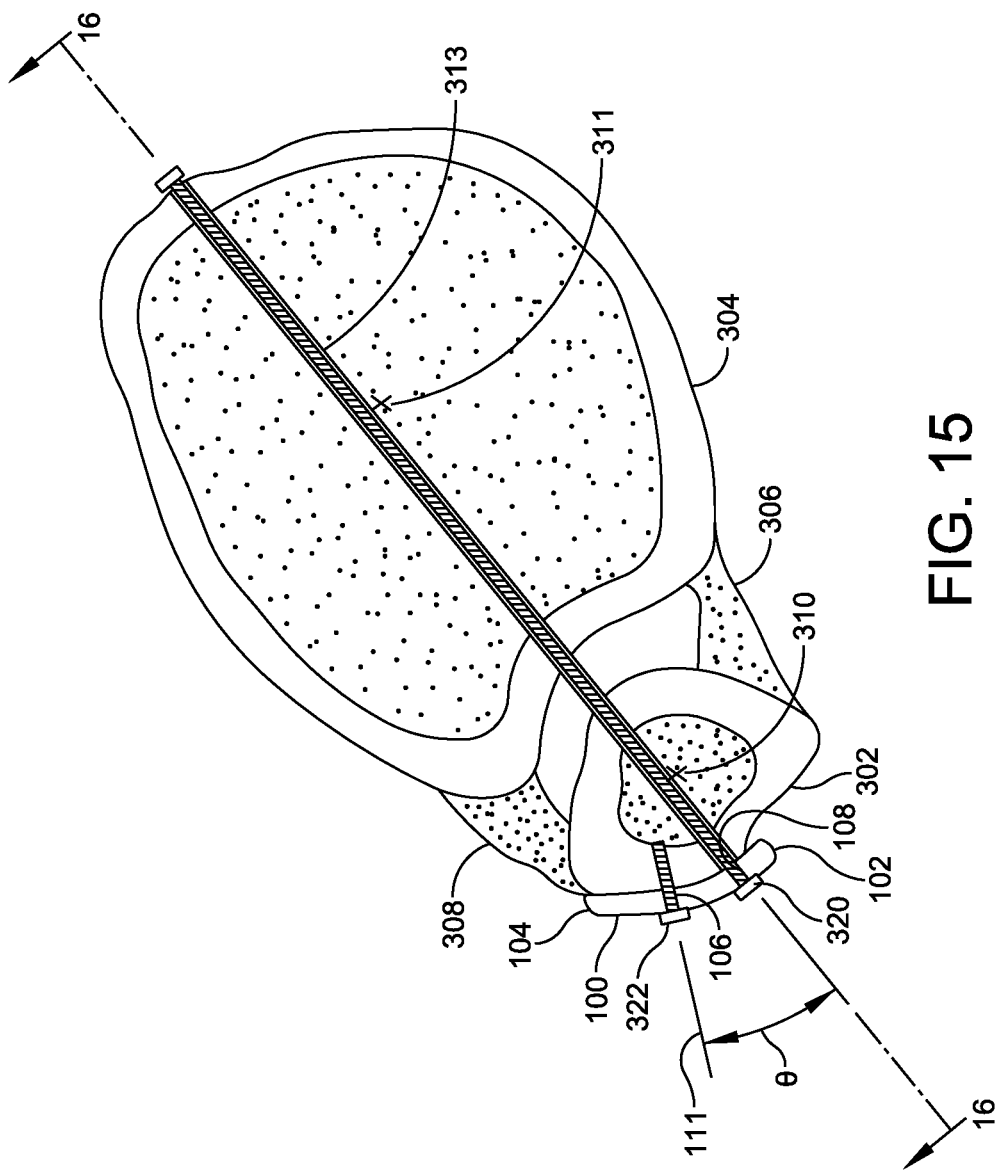
FIG. 15 is a superior cross-sectional view of an ankle with the syndesmosis plate of FIG. 1 implanted thereon.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Surgical treatments for syndesmosis injuries can include implanting a bone plate on the lateral side of the fibula and inserting a fastener (e.g., a syndesmosis screw and/or a button-suture system, such as the "ENDOBUTTON"™ suture sold by Smith & Nephew of Andover, Mass.) through the bone plate, the fibula and the tibia. By tightening the fastener, the surgeon can reduce the syndesmosis.

The bone plate can have a column of holes, including at least two screw-receiving holes and at least one syndesmosis hole, through which the syndesmosis screw or suture is passed. In some cases, the syndesmosis injury is accompanied by a tibia fracture. For treating a combination of syndesmosis and fracture, the implant can be extended in superior and inferior directions to provide bone fixation as well as syndesmosis reduction.

Ideally, when the syndesmosis screw or suture is used, it should be inserted parallel to the tibial plafond in the coronal plane, and thirty degrees relative to the coronal plane of the ankle. This position applies forces to the tibia and fibula, such that a force vector is approximately along a line segment connecting the area centroid of the tibia with an area centroid of the fibular (where the area centroid is determined in a plane parallel to the tibial plafond). This trajectory returns the tibia and fibula to their normal stable relationship. The line passing through the area centroids of the tibia and fibula exits the fibula at the lateral fibular apex, which is just posterior to the anterolateral border of the fibula.

Surgeons generally implant syndesmosis plates on the anterolateral border of the fibula, which is about 20-30 degrees anterior of the lateral fibular apex. This is a position where the plate will not protrude or cause discomfort for the patient. To obtain good syndesmosis reduction, the screws inserted on the anterolateral surface are angulated to point toward the centroid of the tibia, which is about 20-30 degrees from perpendicular to the anterolateral surface. Syndesmosis screws and sutures inserted at this 20-30 degree offset from the lateral fibular apex may provide less stability than similar screws or sutures along the line connecting the area centroids of the tibia and fibula. Also, a screw entering the anterolateral surface and directed toward the centroid of the tibia will be oriented at an angle with respect to the anterolateral surface, so the head of the screw may protrude in an area with little soft tissue covering it. Should the head protrude and cause discomfort to the patient, the surgeon may need to remove the screw.

This disclosure describes examples of syndesmosis plates and fibula fracture plates that allow the surgeon to implant the plates with bone screws on the anterolateral border of the fibula, and insert syndesmosis screws or sutures along the line connecting the centroids (and passing through the lateral fibular apex). The implants make it easier for the surgeon to position and affix the implant to the fibula, while achieving a desired syndesmosis screw or suture alignment for stabile reduction of the syndesmosis.

Figure 16:
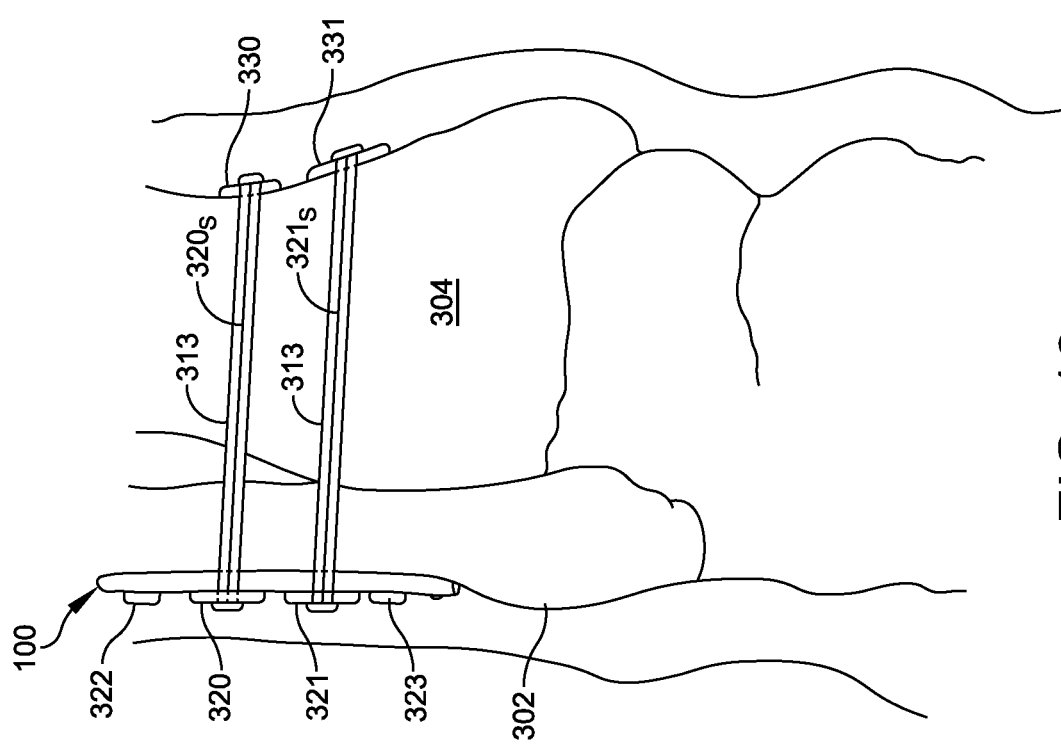
FIG. 16 is a posterior view of the ankle and implant of FIG. 15.

FIGS. 1-8 show a first exemplary embodiment of a syndesmosis plate 100. FIG. 1 is a lateral view of an embodiment of the syndesmosis plate 100. FIG. 2 is an anterior edge view of the syndesmosis plate 100. FIG. 3 is a medial view of the syndesmosis plate 100. FIG. 4 is a cross sectional view of the syndesmosis plate 100 taken along section line 4-4 of FIG. 1. FIG. 5 is a superior end view of the syndesmosis plate 100. FIG. 6 is a posterolateral view of the syndesmosis plate 100. FIG. 7 is a cross-sectional view of the syndesmosis plate 100 taken along section line 7-7 in FIG. 5. FIG. 8 is a cross-sectional view of the syndesmosis plate 100 taken along section line 8-8 in FIG. 6. FIG. 16 is a superior view of a fibula 302 and tibia 304, with the syndesmosis plate 100 implanted on the tibia, and a bone screw or suture 320s and button 320 assembly.

Referring to FIGS. 1, 5 and 6, the syndesmosis plate 100 includes a curved first plate section 102. The curved plate section 102 can have a cross-sectional shape that is circular, elliptical, oval, parabolic, hyperbolic, or logarithmic in shape, or have another curvature. In some embodiments, the curved plate section 102 has circular cross-section with a radius of curvature R1 (shown in FIG. 5) about a longitudinal axis $A_L$ (FIGS. 1 and 5) extending in a longitudinal direction L. In some embodiments, the radius R1 is about 0.5 inch (e.g., 0.4 inch to 0.6 inch), subtending an arc of about 0.25" (e.g., 0.2" to 0.3"), and the longitudinal length of plate section 102 is about 1.5" (e.g., 1.4" to 1.6"). In some embodiments, not shown, the curved plate section 102 is radially offset outward from the non-curved, second plate section 104. In alternate embodiments (not shown), the curved plate section 102 may be disposed on an interior plate portion having a first radius of curvature, with either a non-curved section or a second curved section (having a second, different radius of curvature), extending therefrom. The curved first plate section 102 subtends an angle θ (FIG. 16) from 5 degrees to 45 degrees and is curved to conform to the shape of the lateral surface of the fibula. In some embodiments, the angle θ subtends an angle from 15 to 35 degrees. In some embodiments, the angle θ subtends an angle from 20 to 30 degrees. In other embodiments (not shown), the angle θ is greater than 45 degrees, and the second plate section is shaped to conform to the ridge of the lateral fibular apex. Referring again to FIGS. 1 and 6, the curved first plate section 102 has a first hole 106 and a second hole 107 along a first line segment 111 (FIG. 16) parallel to the longitudinal axis $A_L$. The first hole 106 and the second hole 107 are positioned to receive respective bone screws 322, 323 (FIG. 17) for attaching the syndesmosis plate 100 to a first curved surface of a bone (e.g., fibula) 302 (FIGS. 16, 17) having a syndesmosis. Alternately, the first hole 106 and the second hole 107 may be disposed along a first line segment and a second line segment, wherein the first line segment and the second line segment are both parallel to the longitudinal axis, and the second line segment is offset in a tangential direction—orthogonal to the radial direction—from the first line segment. The syndesmosis includes the posterior talofibular ligament 306 and anterior talofibular ligament 308 (FIG. 16). In some embodiments, the first hole 106 and the second hole 107 are locking screw holes for receiving bone screws to secure the syndesmosis plate 100 on the lateral surface of the fibula 302.

Referring again to FIGS. 1 and 6, a second plate section 104 extends continuously from the curved first plate section 102. The second plate section 104 has at least a third hole 108 offset from the first line segment 111 FIG. 16). The third hole 108 is configured to receive at least one (locking or non-locking) screw or button 320 (FIG. 17) for holding a suture 320s at a position offset from the first line segment by the angle θ, for reducing the syndesmosis. In some embodiment, the third hole 108 is positioned to be offset in a direction that is anterior or posterior from the first hole 106 and the second hole 107 in a case where the longitudinal axis $A_L$ is aligned along a superior-inferior direction of the fibula. Some embodiments include one or more additional holes 109 in the second plate section 104. In some embodiments, the third hole 108 and fourth hole 109 are non-locking holes for receiving a non-locking screw or a suture system, such as a button 320 and suture 320s. In some embodiments, the third hole 108 and fourth hole 109 are locking holes for receiving syndesmosis screws. In some embodiments, the locking or non-locking holes 108, 109 have a counterbore about 0.010 inch to 0.015 inch deep for seating the head of the screw or button 320.

In some embodiments, the second plate section 104 is flat and extends for a length 312, as shown in FIGS. 5 and 8. For example, the length 312 can be about 0.13 inch (e.g., from 0.12 to 0.14 inch). In some embodiments (not shown), the second plate section 104 is curved with a circular cross-section and has the same radius of curvature as the first plate section. In other embodiments (not shown), the second plate section 104 extends from a second outer plate edge, inward/medially, towards the first plate section 102. In other embodiments (not shown), the second plate section is curved to conform to the lateral fibular apex. In other embodiments (not shown), the second plate section has a notch or rib to accommodate the posterior ridge of the fibula.

In some embodiments, as shown in FIGS. 1 and 6, the syndesmosis plate 100 has a first edge with a convex portion 104e, and the third hole 108 is located adjacent the convex portion 104e of the first edge.

In some embodiments, as shown in FIGS. 1 and 6, the syndesmosis plate 100 has a second edge with a concave portion 110, and the first hole 106 and the second hole 107 are located adjacent the end portions of the second edge excluding the concave portion 110. In some embodiments, the concave edge has a radius from about 1.5 inch to about 3 inch.

Figure 17:
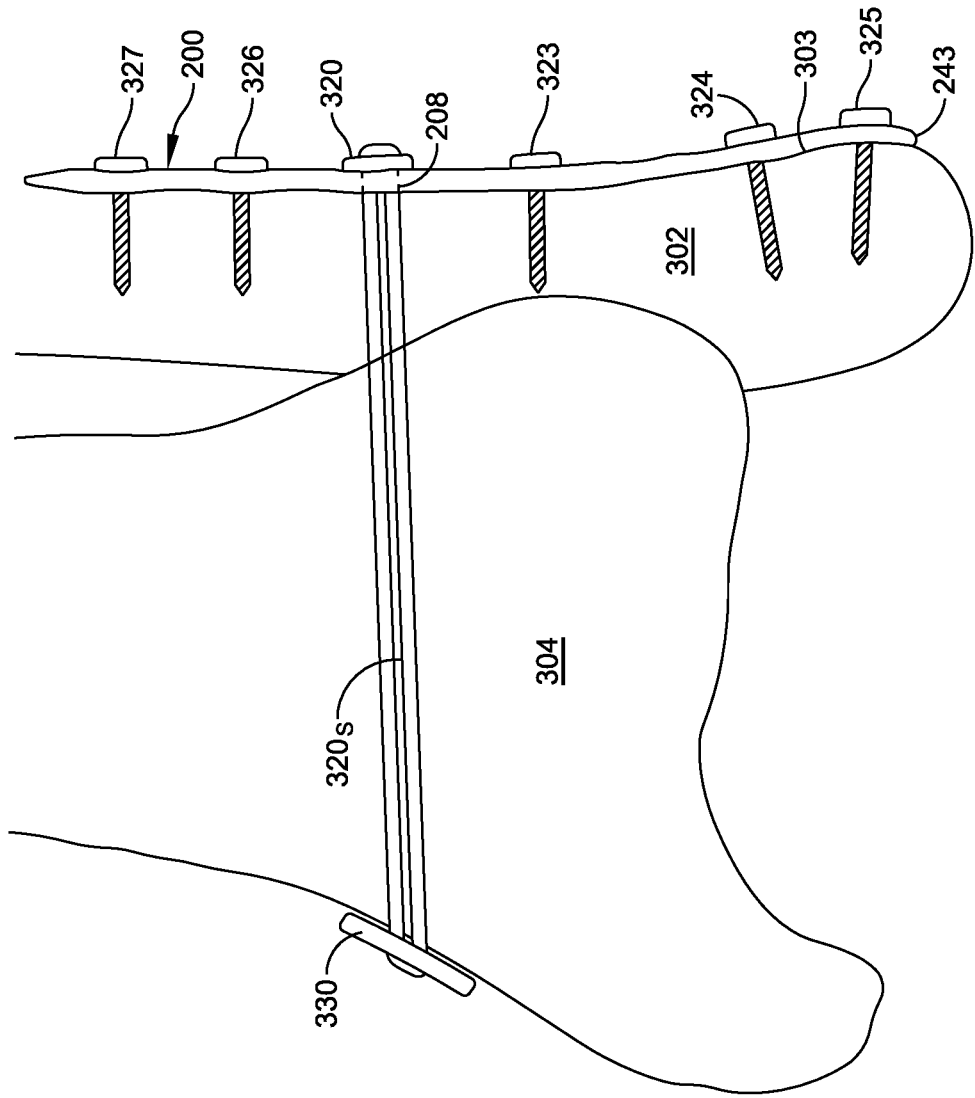
FIG. 17 is an anterior view of an ankle with the fibula fracture plate of FIG. 10 implanted thereon with a suture for syndesmosis reduction.

FIG. 16 is a superior cross-sectional view of the fibula 302 and tibia 304 taken in a plane parallel to the tibial plafond. FIG. 17 is a cross-sectional view taken along section line 17-17 of FIG. 16. The syndesmosis plate 100 is secured to the anterolateral surface of the fibula by bone screws 322 through the holes 106, 107 along the line segment 111. The surgeon drills holes 313 which is aligned with the syndesmosis hole 108 and passes through the centroid 310 of the fibula 302 and the centroid 311 of the tibia 304. The syndesmosis hole 108 is offset from the screws 322 by the angle θ, so the syndesmosis holes are aligned with the lateral apex of the fibula 302. The surgeon inserts a button 320 and suture 320s assembly with a retainer 330 through the hole drilled through the fibula 302 and tibia 304. In other embodiments (not shown), the surgeon inserts a syndesmosis screw through each syndesmosis hole 108, 109, the fibula 302 and the tibia 304.

In FIGS. 16 and 17, the syndesmosis plate 100 is positioned with the first plate section 102 on the anterolateral surface of the fibula 302, and the second plate section 104 extending in the posterior direction to the lateral face. The same syndesmosis plate 100 can also be flipped and positioned with the first plate section 102 on the posterolateral surface of the fibula 302, and the second plate section 104 extending in the anterior direction to the lateral face.

FIG. 9 is a lateral view of a variation of the syndesmosis plate. The general form of the plate 150 is the same as syndesmosis plate 100 of FIGS. 1-8, except that plate 150 has a straight edge 160 instead of a curved edge 110 (as shown in FIGS. 1-8). The shape of the edges can be varied.

FIGS. 10-15 and 18 show an embodiment of a fibula fracture plate 200. The implant system has a bone plate 200 comprising a curved first plate section 202 (FIG. 12) having a radius of curvature R3 about a longitudinal axis $A_{L1}$ (FIG. 14), extending in a longitudinal direction, the curved first plate section 202 subtends an angle θ1 (FIG. 14) from 5 degrees to 45 degrees, e.g., from 25-35 degrees. The curved first plate section 202 has a first hole 206 and a second hole 207 arranged along a first line segment 211 parallel to the longitudinal axis $A_{L1}$. The first hole 206 and the second hole 207 are positioned to receive respective bone screws 324-327 (see FIG. 18) for attaching the implant 200 to a curved surface of a fibula 302 that extends to an ankle having a syndesmosis. In some embodiments, the first hole and the second hole are locking screw holes, and the third hole and the fourth hole are non-locking holes.

A second plate section 204 (FIG. 12) extends continuously from the curved first plate section 202. In some embodiments, the second plate section 204 of the implant 200 has a first edge 241 with a convex portion, and the third hole 208 and the fourth hole 209 are each located adjacent the convex portion of the first edge 241. The second plate section has a third hole 208 offset from the first line segment 211. In some embodiment, the third hole 208 is positioned to be offset in a direction that is anterior or posterior from the first hole 206 and the second hole 207 in a case where the longitudinal axis $A_L$ is aligned along a superior-inferior direction of the fibula. The third hole 208 is configured to receive at least one (locking or non-locking) bone screw or button for holding a suture 320s. In some embodiments, the third hole 208 and fourth hole 209 are non-locking holes for receiving a non-locking screw or a suture system, such as a button 320 and suture 320s. In some embodiments, the third hole 208 and fourth hole 209 are locking holes for receiving syndesmosis screws. In some embodiments, the third hole 208 is configured to receive the bone screw or a button for positioning the at least one suture 320s at a lateral apex of the fibula (at the same location shown for syndesmosis plate 100 in FIG. 16) for reducing the syndesmosis. In some embodiments, the holes 208, 209 have a counterbore about 0.010 inch to 0.015 inch deep for seating the head of the screw or button 320. In some embodiments, the implant 200 has a second edge with a concave portion 239, and the first hole 206 and the second hole 207 are located adjacent portions of the second edge excluding the concave portion 239.

The fibula fracture plate 200 has a third plate section 252 (FIG. 12) located adjacent the second hole 207 and having a concave region shaped to conform to a lateral malleolus 303 (FIG. 18) of the fibula 302. In some embodiments, as shown in FIG. 13, the third plate section 252 is offset from the curved first plate section 202 and the second plate section 204 in the radial direction, to accommodate the lateral malleolus 303. The third plate section 252 has at least n additional hole 232-235 (FIGS. 11, 12), positioned to receive an additional bone screw(s) 324-327. In some embodiments, the third plate section has one or more additional holes positioned to receive one or more additional bone screws adjacent a plurality of locations on the lateral malleolus. In some embodiments, the fibula fracture plate has a superior section opposite the third section. The superior section can include additional screw holes 221, 222 and provides additional support and fixation for a fibula fracture.

The number of syndesmosis holes 208, 209 is not limited to two, and can be at least one or more holes. The number and configuration of screw holes in the fibula fracture plate are not limited to the configuration of FIGS. 11-12 and can be varied. Additionally, the shape of the perimeter of the fibula fracture plate 200 can be varied. For example, the perimeter in near the screw holes 221, 222 has an undulating shape with a neck 203, which allows a surgeon to drive a screw into the fibula adjacent to the implant 200 in the scallop (neck) 203 at a different angle for additional fixation and/or enhanced stability. For example, the surgeon can insert the screws so that the distal ends of the screws (opposite the heads) diverge from each other. The scallops (necks) also allow for the surgeon to contour or bend the plate about a tangential axis—orthogonal to the radial and longitudinal axes—to follow the shape of the lateral malleolus of the fibula, for example. In some embodiments, the third plate section 252 has one or more additional undulating curves to provide additional sites at which the surgeon can optionally drive additional screws if appropriate for a particular injury. Further, the shape of plate edges may vary. The plate edges may be rounded, rectangular with rounded corners, or plate edges may have defined corners.

Figure 18:
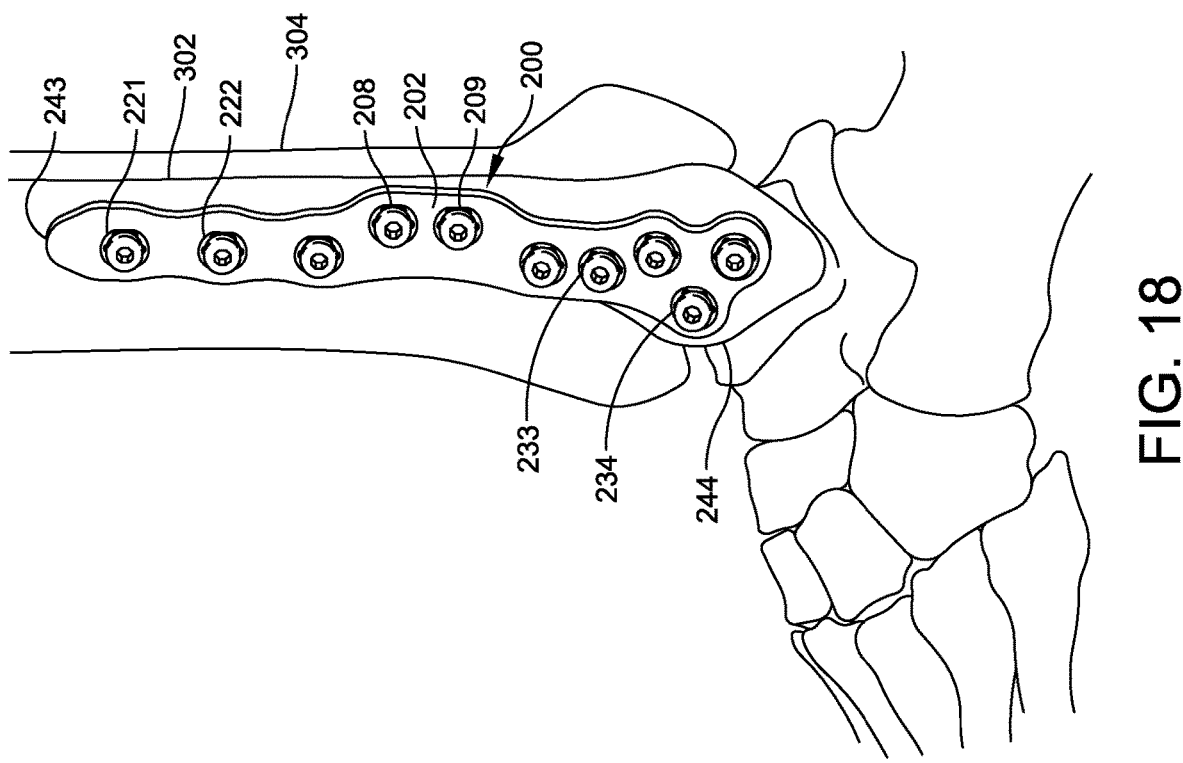
FIG. 18 is a lateral view of an ankle with the fibula fracture plate of FIG. 10 implanted thereon with screws for syndesmosis reduction.

As shown in FIG. 18, at least one syndesmosis screw or suture $320s$ is inserted through a lateral-medial hole through the fibula 302 and tibia 304. The syndesmosis screw or suture $320s$ performs the same function in the fracture plate 200 as discussed above with respect to the syndesmosis plate 100, and is not repeated, for brevity.

FIGS. 16-17 show a method of using the syndesmosis plate 100, and FIG. 18 shows a method of using the fibula fracture plate 200.

As shown in FIGS. 16-17, the method includes positioning a bone plate (e.g., syndesmosis plate 100) on an anterolateral side of a fibula 302 having a syndesmosis 306, 308. The syndesmosis plate 100 has a curved first plate section 102 (anterolateral plate section) having a radius of curvature R1 about a longitudinal axis $A_L$ extending in a longitudinal direction L. The curved first plate section 102 subtends an angle θ from 5 degrees to 45 degrees. The curved first plate section has a first superior hole 106 and a first inferior hole 107 along a first line segment 111 parallel to the longitudinal axis $A_L$. The first superior hole 106 and the first inferior hole 107 are positioned to receive respective bone screws 322 for attaching the syndesmosis plate 100 to an anterolateral surface of the fibula 302.

The syndesmosis plate 100 is positioned so that a lateral plate section (e.g., second plate section 104), extending continuously from the curved first plate section 102, has at least one syndesmosis hole 108, 109 offset in a posterior direction from the first line segment 111. The positioning is performed so the lateral plate section does not overhang a posterior ridge of the fibula, to avoid patient discomfort. The at least one syndesmosis hole 108, 109 is configured to receive at least one screw or button 320 for holding at least one suture $320s$ at a lateral apex of the fibula 302. If the implant is a fibula fracture plate 200, then the implant 200 is positioned so that an inferior plate section (third plate section 252) is located inferior to the first inferior hole 208 and the concave region 239 conforms to the lateral malleolus 303 of the fibula 302.

The surgeon drills through the holes 106, 107 for implanting the syndesmosis plate 100 and inserts bone screws to hold the plate in place. If the fibula fracture plate 200 (FIG. 18) is being implanted, then additional bone screws 323-327 are inserted at this time. Then the surgeon can partially pre-drill the syndesmosis holes (e.g., about 1" into the bone) with a k-wire and check the trajectory of the syndesmosis hole by fluoroscope. If the trajectory is not correct, the surgeon re-drills the syndesmosis hole to change the trajectory, and checks using another X-ray or fluoroscopic image. If the trajectory is proper, the surgeon completes the pre-drilling, including drilling the syndesmosis holes through the fibula and tibia.

Once the syndesmosis holes are drilled, the surgeon drives the bone screws or suture into the syndesmosis holes to reduce the syndesmosis.

As shown in FIG. 17, the surgeon then inserts the at least one syndesmosis screw or suture through the at least one syndesmosis hole, the fibula, and a centroid of a tibia adjacent the fibula. If a button-suture system is used, the surgeon inserts the suture through the holes in the fibular and tibia, and attaches the suture to the retaining device 330 on the medial side of the tibia.

The surgeon then reduces the syndesmosis by advancing the syndesmosis screw or tensioning the suture to reduce the syndesmosis.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:
   implanting a bone plate on an anterolateral side of a fibula having a syndesmosis, wherein the implanting is performed in the absence of a lateral plate section of the bone plate overhanging a posterior ridge of the fibula, the bone plate having:
   a curved plate section having a curvature extending in a longitudinal direction, the curved plate section having a first superior hole and a first inferior hole, the first superior hole and the first inferior hole positioned to receive respective bone screws for attaching the implant to an anterolateral surface of a fibula that extends to an ankle, and
   the lateral plate section extending continuously from the curved plate section, the lateral plate section having at least a third hole offset in an anterior or posterior direction from the first superior hole and the first inferior hole, the at least third hole is configured to receive at least one of a screw or a button for holding at least one suture at a lateral apex of the fibula;

driving a first screw into the anterolateral side of the fibula through the first superior hole at a first angle;

driving a second screw into the anterolateral side of the fibula through the first inferior hole at a second angle that diverges from the first angle;

pre-drilling, in part, a syndesmosis hole and checking a trajectory of the syndesmosis hole, wherein the checking of the trajectory of the syndesmosis hole includes:

checking at least one of an X-ray or fluoroscopic image for a correct trajectory of the syndesmosis hole;

in response to an incorrect trajectory, re-drilling the syndesmosis hole to change the trajectory, and re-checking the trajectory using another X-ray or fluoroscopic image;

in response to a correct trajectory, completing the pre-drilling by drilling the syndesmosis hole through the fibula and a tibia adjacent the fibula;

inserting the at least one suture through the at least third hole and the syndesmosis hole; and tensioning the suture to reduce the syndesmosis.

2. The method of claim 1, wherein the at least third hole is separated from the first superior hole and the first inferior hole by an angle in a range from 25 degrees to 35 degrees.

3. The method of claim 1, wherein the inserting step inserts the at least one suture so the suture passes through an area centroid of the fibula and an area centroid of the tibia.

4. The method of claim 1, wherein the implanting step includes inserting bone screws through the first superior hole and the first inferior hole in the curved plate section, and the suture is separated from the bone screws by an angle in a range from 25 degrees to 35 degrees in a plane parallel to a tibial plafond of the tibia.

* * * * *